US 9,869,635 B2

(12) United States Patent
Stengel et al.

(10) Patent No.: US 9,869,635 B2
(45) Date of Patent: Jan. 16, 2018

(54) MEASURING DEVICE FOR MEASURING PARTICULATE MATTER CONCENTRATIONS USING SCATTERED LIGHT AND METHOD FOR MONITORING THE MEASURING DEVICE

(75) Inventors: Karl Stengel, Deizisau (DE); Guenter Nobis, Nuertingen (DE); Gerhard Haaga, Ohmden (DE); Michael Neuendorf, Plochingen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 423 days.

(21) Appl. No.: 13/978,086

(22) PCT Filed: Dec. 27, 2011

(86) PCT No.: PCT/EP2011/074060
§ 371 (c)(1),
(2), (4) Date: Sep. 5, 2013

(87) PCT Pub. No.: WO2012/093050
PCT Pub. Date: Jul. 12, 2012

(65) Prior Publication Data
US 2013/0335739 A1     Dec. 19, 2013

(30) Foreign Application Priority Data

Jan. 4, 2011   (DE) .................... 10 2011 002 421

(51) Int. Cl.
*G01N 21/49*   (2006.01)
*G01N 15/06*   (2006.01)
(Continued)

(52) U.S. Cl.
CPC ............. *G01N 21/49* (2013.01); *G01N 15/06* (2013.01); *G01N 21/274* (2013.01);
(Continued)

(58) Field of Classification Search
CPC ........... G01N 15/0255; G01N 15/0272; G01N 15/0643
(Continued)

(56) References Cited

U.S. PATENT DOCUMENTS 3,234,846 A * 2/1966 Cropper ............... G01N 21/532
                                                       250/239
4,017,186 A     4/1977 Shofner et al.
(Continued)

FOREIGN PATENT DOCUMENTS

| CN | 101187617 | 5/2008 |
|---|---|---|
| CN | 201191264 | 2/2009 |
| DE | 10 2010 002 423 | 9/2011 |

*Primary Examiner* — Dominic J Bologna
(74) *Attorney, Agent, or Firm* — Norton Rose Fulbright US LLP; Gerard Messina

(57) ABSTRACT

A measuring unit for measuring a particulate concentration in exhaust gases using scattered light includes a measuring chamber, at least one light source and at least one light sensor, the measuring chamber being situated in the optical path of the light source; and the light sensor records the light scattered by the particulates in the measuring chamber. To detect the intensity of light beam that is relevant for a precise particulate measurement, a monitoring device is provided to detect the intensity of the light beam with the aid of a scattered radiation. The intensity of the light beam is recorded using a monitoring measurement, by ascertaining a scattered radiation and comparing it to a specified reference value for the scattered radiation. With the aid of the comparison, the intensity of the light source is regulated correspondingly and/or the measuring result of the particulate measurement is correspondingly corrected.

23 Claims, 3 Drawing Sheets

(51) Int. Cl.
    *G01N 21/27*         (2006.01)
    *G01N 21/47*         (2006.01)
    *G01N 21/51*         (2006.01)
    *G01N 21/53*         (2006.01)

(52) U.S. Cl.
    CPC ......... *G01N 21/4785* (2013.01); *G01N 21/51* (2013.01); *G01N 21/53* (2013.01)

(58) Field of Classification Search
    USPC ................................................ 356/336–443
    See application file for complete search history.

(56) References Cited

U.S. PATENT DOCUMENTS

| | | | |
|---|---|---|---|
| 4,053,229 A | | 10/1977 | McCluney |
| 4,907,884 A | | 3/1990 | Philips et al. |
| 5,084,629 A | * | 1/1992 | Petralli .................. G01N 21/53 |
| | | | 356/343 |
| 5,340,987 A | * | 8/1994 | Eckles ............... G01N 21/3504 |
| | | | 250/343 |
| 5,777,748 A | * | 7/1998 | Stengel ................ G01N 21/532 |
| | | | 250/574 |
| 7,682,426 B2 | * | 3/2010 | Burtscher et al. ......... 73/863.12 |
| 8,208,143 B2 | * | 6/2012 | Goto et al. .................... 356/432 |
| 2008/0212094 A1 | * | 9/2008 | Altobelli ................. A61B 5/08 |
| | | | 356/338 |

\* cited by examiner

MEASURING DEVICE FOR MEASURING PARTICULATE MATTER CONCENTRATIONS USING SCATTERED LIGHT AND METHOD FOR MONITORING THE MEASURING DEVICE

FIELD OF THE INVENTION

The present invention relates to a measuring device for measuring the particulate concentration in exhaust gases using scattered light, and a method for monitoring the measuring device.

BACKGROUND INFORMATION

The use of scattered light methods for measuring the concentration of particles in exhaust gases and other colloids are believed to be in the related art.

A measuring device provided for this usually includes a fast light source, such as a laser, which radiates light into a measuring chamber through which the colloid to be measured is conducted. The measuring chamber has at least one light sensor assigned to it which detects light, that has been scattered by the particulates present in the colloid. In order to check the proper functioning of such a measuring device and to calibrate the measuring device, it is necessary to set a specified state in the measuring chamber at which the incident light is scattered in a defined and known manner. Measuring devices, that are used for official measurements, are covered by official calibration duty, whereby the necessity for supplying accurate measurement results with high reliability increases even further. Such a measuring unit is discussed in German Patent Application 10 2010 002 423.6.

SUMMARY OF THE INVENTION

It is an object of the present invention to provide a measuring unit and a method using which a simple, reliable and accurate checking of the light beam in the measuring chamber for measuring particulate concentrations is possible.

This object may be attained using the characterizing features of the independent claims, in that a monitoring device is provided in the optical path of the light beam to detect the intensity of the light beam in the measuring chamber, a defined scattered radiation of the light beam being produced, recorded and evaluated, by comparing the defined scattered radiation to a reference value of the scattered radiation. The radiation of the light source impinges essentially unattenuated upon the monitoring device. Using the measuring unit according to the present invention and the method according to the present invention monitoring and regulating of the intensity of the light beam in the measuring chamber of the measuring unit may be done. It also may be provided, with that, to detect soiling of the light source and/or the light sensors.

The intensity of the light beam, and also the radiation intensity is the proportion of the overall radiation power that is emitted by the light source in one spatial direction, in the present case, in the direction of the measuring chamber.

The features of the further descriptions herein provide advantageous further refinements.

The monitoring device expediently has a scattered light member and an additional light sensor, upon irradiation by light of the light source, the scattered light member emitting a scattered light radiation having a specified intensity, and the additional light sensor records the radiation of light scattered by the scattered light member. The additional light sensor or monitor sensor supplies a signal, which is directly proportional to the intensity of the light beam in the measuring chamber. This signal may therefor be used for monitoring and/or regulating the intensity of the light beam in the measuring chamber. In addition or alternatively, a correction is thereby possible of the actual measuring signal of the light sensors.

According to advantageous specific embodiments, the scattered light member is situated in a monitoring position in the radiation direction of the light source outside the measuring chamber, or in a monitoring position inside the measuring chamber or inside the measuring chamber in a positioning device with which the scattered light member is able to be displaced from a calibrating position to the monitoring position. The situation of the scattered light member expediently takes place in suitable accommodation devices that are positioned in a calibrating position and/or in a monitoring position.

Furthermore, it is expedient to assign to the additional light sensor an evaluation device for the ascertainment and/or representation of the scattered light radiation taken up from the additional light sensor.

The measuring unit advantageously has a microcontroller, which compares the intensity of the scattered radiation recorded by the additional light sensor, and ascertained by the additional evaluation device, to a specified reference value for the scattered radiation and determines from this the intensity of the light beam in the measuring chamber. In this context, the microcontroller may be connected to the evaluation device and the light source and may include a control system which regulates the intensity of the light source to the specified reference value of the scattered radiation. Furthermore, the microcontroller may be connected to the evaluation devices of the measuring unit, in order to correct the result of a preceding exhaust gas measurement. For this, the microcontroller has a correction algorithm, using which the result of the evaluation devices of the measuring unit is corrected, with the aid of the deviation of the ascertained intensity of the scattered radiation from the specified reference value for the scattered radiation.

In addition, the scattered light member may simultaneously be used in a calibrating device as a scattered light member, or vice versa, the scattered light member of a present calibrating device may be used as a scattered light member in the monitoring device. A relatively simple arrangement only is required for the exchange, suitable accommodation devices in the calibrating position and in the monitoring position being able to be provided for the accommodation of the scattered light members.

For checking the light beam in the measuring chamber of the measuring unit, consequently a monitoring measurement is carried out before or after the particulate measurement. For this purpose, the intensity of the scattered radiation ascertained by the monitoring device is compared to the specified reference value for this scattered radiation. According to a first alternative, the light intensity of the light source is corrected to the specified reference value of the scattered radiation. According to a second alternative, the result of the measurement of the particulate concentration is corrected with the aid of the deviation of the scattered radiation produced from the specified reference value for this scattered radiation.

Exemplary embodiments of the present invention are illustrated in the drawings and are explained in greater detail in the following description.

DETAILED DESCRIPTION

Figure 1:
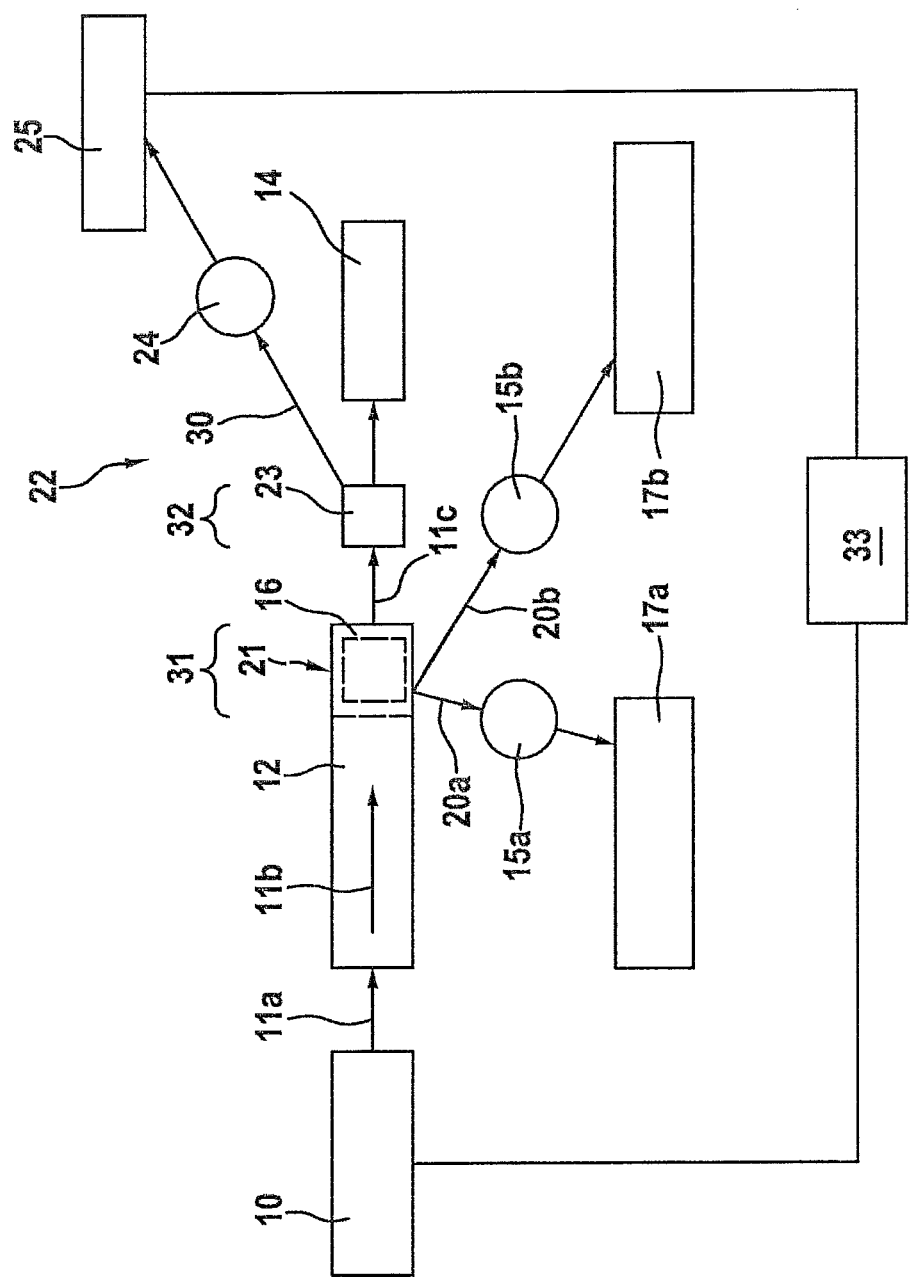
FIG. 1 shows a schematic of a measuring unit for measuring a particulate concentration using scattered light according to a first exemplary embodiment.
Figure 2:
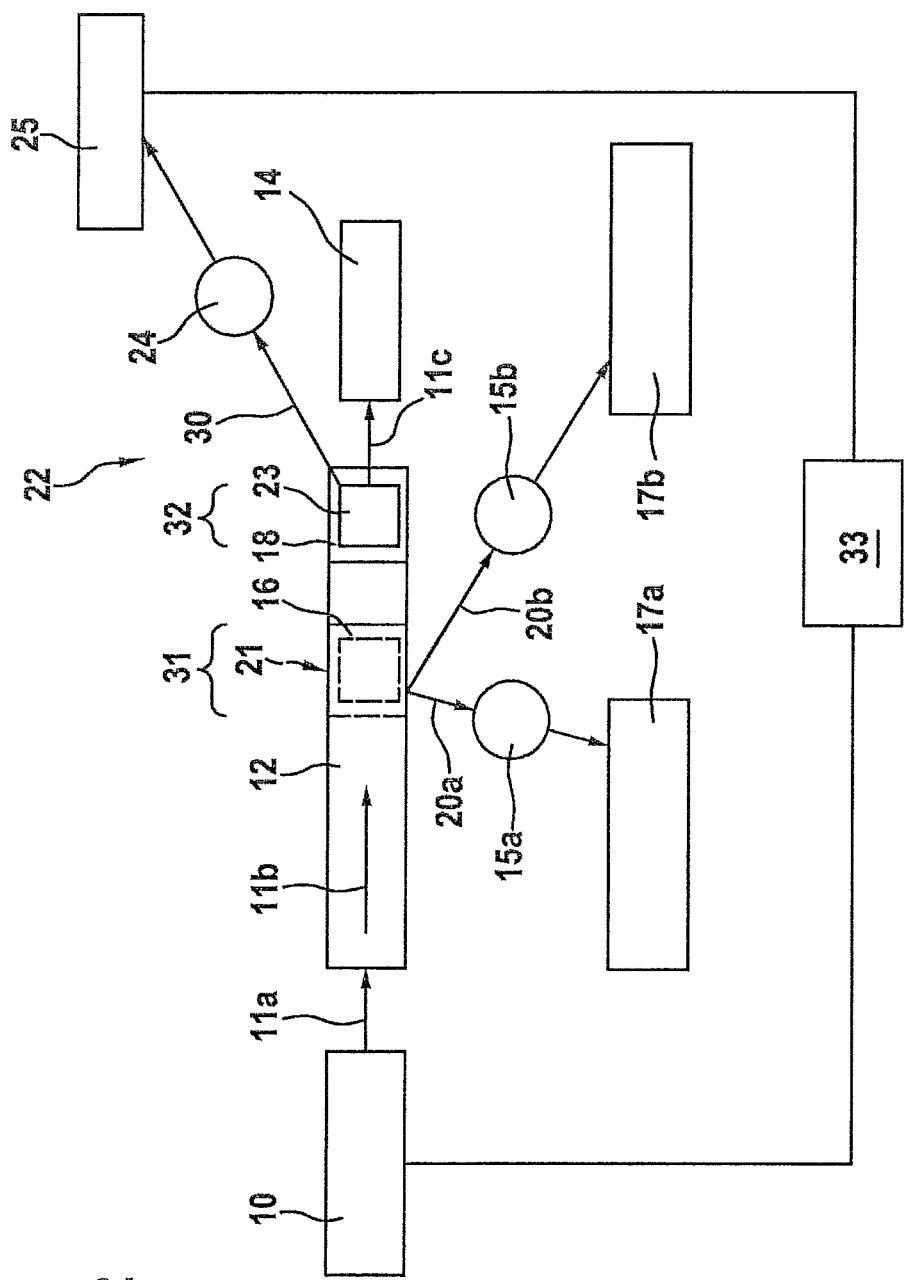
FIG. 2 shows a schematic of a measuring unit for measuring a particulate concentration using scattered light according to a second exemplary embodiment.
Figure 3:
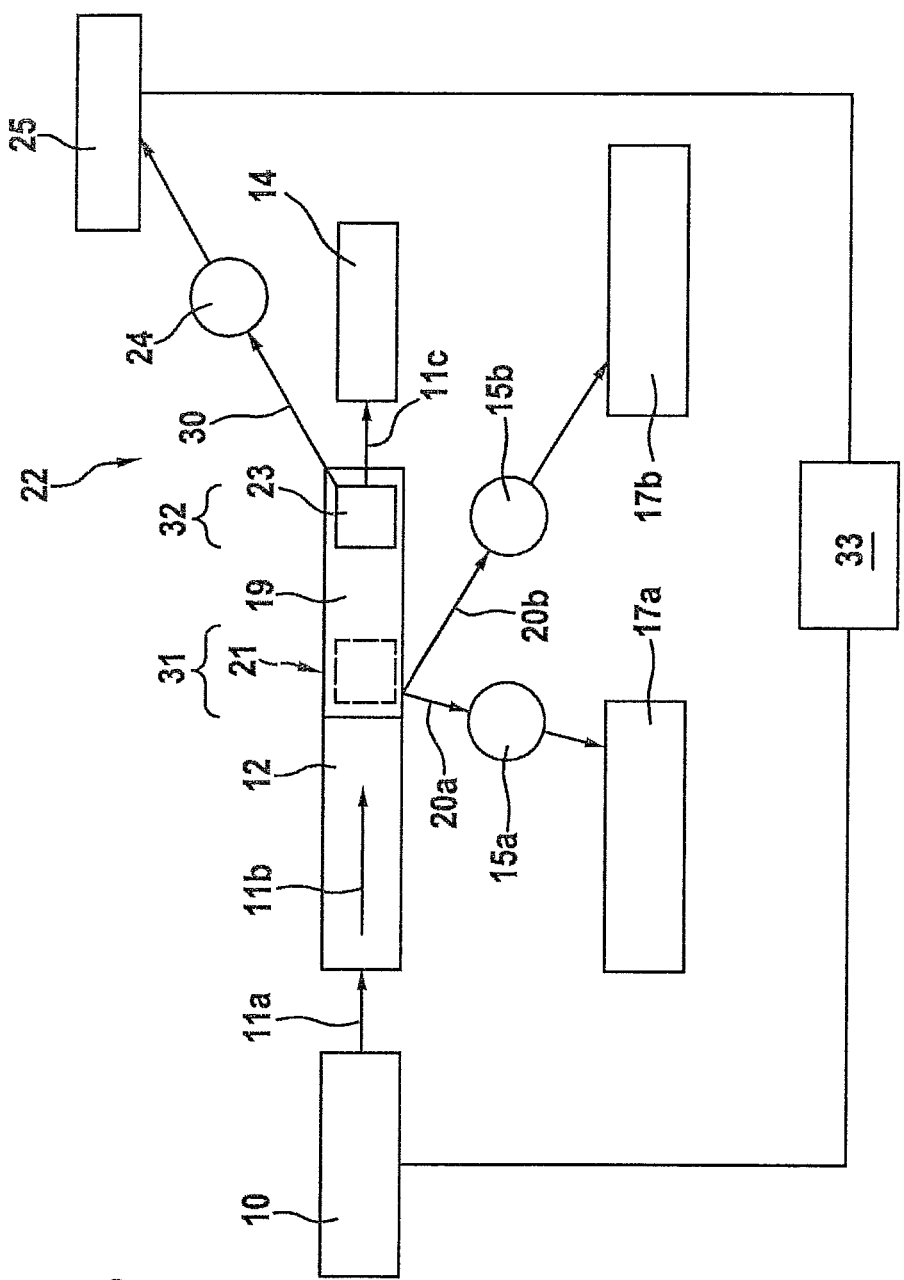
FIG. 3 shows a schematic of a measuring unit for measuring a particulate concentration using scattered light according to a third exemplary embodiment.

The measuring unit shown in FIGS. 1, 2 and 3 is used for measuring a particulate concentration in exhaust gases or other colloids, particularly in exhaust gases of motor vehicles using scattered light. The measuring unit has a measuring chamber 12, through which exhaust gas is conducted from a motor vehicle, via inlets and outlets that are not shown. In the process, the exhaust gas is able to be guided, by the pressure generated by the engine of the motor vehicle, the so-called exhaust gas back pressure, through measuring chamber 12. A pump, that is not shown, may be provided additionally, to support the exhaust gas flow through measuring chamber 12.

The measuring unit has at least one light source 10, which is developed as a laser light source, for example. In the switched-on state, light source 10 generates a light beam 11a, which is coupled into measuring chamber 12 using a defined intensity and runs within measuring chamber 12 as a light beam 11b. Light beam 11b exits from measuring chamber 12 as an additional light beam 11c, and after measuring chamber 12, it impinges upon a radiation absorber 14 (beam dump) situated there, in which the non-scattered or partially absorbed light of light source 10 is completely absorbed or nullified.

At least one, but in the exemplary embodiments shown in FIGS. 1, 2 and 3, in each case, two light sensors 15a, 15b are assigned to measuring chamber 12, which detect light from light beam 11b that has been scattered by the exhaust gas flow conducted through measuring chamber 12, as scattered radiations 20a and 20b. In the schematic representation of FIGS. 1, 2 and 3, light source 10 and light sensors 15a, 15b, for reasons of greater clarity, are shown outside measuring chamber 12, although, in reality, they are at least partially situated within or directly at measuring chamber 12.

Light sensors 15a, 15b may be situated at different angles with respect to the beam direction of the light radiation of irradiated light beam 11a, so that they are able to detect scattered light at different angles as scattered radiations 20a and 20b. The electrical signals emitted by light sensors 15a, 15b are supplied to one or more electronic amplifying and evaluating devices 17a, 17b, which evaluate the signals and ascertain and output the concentration of particulates in the gas flow conducted through measuring chamber 12.

In order to obtain measuring results having high accuracy which correspond, for example, to high legal requirements, light sensors 15a, 15b of the measuring unit have to be calibrated regularly, and the intensity of the light source has to be monitored. To calibrate light sensors 15a, 15b, a calibrating measurement is carried out. For this purpose, in measuring chamber 12 in a specified calibration position 31 with which light sensors 15a and 15b are associated, a calibrating device having a scattered light member 21 is used, the scattered light member 21 generating defined scattering radiations 20a and 20b, which correspond to a specified, known particle concentration. Scattered light member 21 of the calibrating device in calibrating position 31 is indicated in FIGS. 1, 2 and 3 in each case by dashed lines. At a defined intensity of light beam 11b, scattered light member 21 supplies scattered light radiation 20a and 20b at a defined intensity. The arrangement of such a scattered light member 21 is referred to in German Patent Application 10 2010 002 423.6.

To the calibration device, there further belong light sensors 15a, 15b present in the measuring unit and appertaining evaluation devices 17a, 17b, so that the light scattered by scattered light member 21 in measuring chamber 12 is recorded having scattered light radiations 20a and 20b by light sensors 15a, 15b and the particulate concentration associated with scattered light member 21 is ascertained by evaluation devices 17a, 17b. Light source 10 and/or evaluation devices 17a, 17b are adjusted in such a way that evaluation devices 17a, 17b output the specified, known particulate concentration as a result of the calibrating measurement.

According to the present invention, a monitoring measurement is undertaken of light beam 11b running in measuring chamber 12. In addition, a monitoring device 22 is provided for monitoring the intensity of light beam 11b, which includes an additional scattered light member 23, at least one additional light sensor 24 and at least one additional evaluation device 25. Additional scattered light member 23 is situated in this context in the optical path of light source 10 in such a way that the radiation or light beam 11b of light source 10 impinges, essentially unattenuated, upon scattered light member 23. Additional light sensor 24 may also be designated as a monitor sensor, because of its monitoring function. Additional light sensor 24 is situated at a defined angle to the beam direction of light beam 11a, 11b and 11c. Additional scattered light member 23 is situated in a defined monitoring position 32, which is different from calibrating position 31, monitoring position 32 in the beam direction of light source 10 may be behind calibrating position 31. At a defined intensity of light beam 11c (FIG. 1) or 11b (FIG. 2 or 3), scattered light member 23 supplies a scattered radiation 30 also having a defined intensity, which is recorded by additional light sensor 24, the signal of additional light sensor 24 being evaluated by additional evaluation device 25.

The intensity of scattered radiation 30 may deviate from the intensity of scattered radiation 20a and 20b at the calibrating measurement as a function of the angle between light beam 11b or 11c. If the calibrating measurement for calibrating the calibrating unit and a first monitoring measurement are carried out directly one after the other, and the value of the first monitoring measurement is stored as a reference value of scattered radiation 30, the intensity of light beam 11b and/or the result of the particulate measurement with the reference value may be returned directly to the calibrated state.

As an additional scattered light member 23, scattered light member 21 of the calibrating device may be used, and, in reverse, additional scattered light member 23 of monitoring device 22 may be used as scattered light member 21 of the calibrating device.

The measuring unit also has a microcontroller 33, which compares the intensity of scattered radiation 30, recorded by additional light sensor 23 and ascertained by additional evaluation device 24 to a specified reference value for scattered radiation 30. From the comparison, the intensity of light beam 11b in measuring chamber 12 is ascertained. In the present exemplary embodiments, only one connection of microcontroller 33 to additional evaluation device 25 of monitoring device 22 is shown and one connection to light source 10.

The signal generated by additional light sensor 24 is passed on to additional evaluation device 25 for ascertaining and/or representing the signal strength In the second exemof additional light sensor 24. Using evaluation device 25, the intensity of scattered radiation 30 is ascertained, so that, using monitoring device 22 and microcontroller 33, the intensity of light source 10 is able to be monitored and regulated. Based on the defined physical properties of scattered light member 23 in defined monitoring position 32 and the defined situation of light sensor 24 as well as while taking into account the results of the preceding calibrating measurement for calibrating the measuring unit, the intensity of light beam 11b in measuring chamber 12 relevant for the particulate measurement is able to be ascertained, monitored and regulated. Furthermore, using the result of the monitoring measurement, the result of one or more particulate measurements carried out between the monitoring measurements may be automatically corrected with reference to the calibrating state.

The monitoring measurement in monitoring position 32 is expediently carried out when measuring chamber 12 is empty and contains no scattering particulate and also no scattering member 21 of the calibrating device, so that there is essentially no light scattering occurring in measuring chamber 12.

According to the first exemplary embodiment in FIG. 1, in measuring chamber 12 in calibrating position 31, a first accommodating device 16 is present for accommodating scattered light member 21 of the calibrating device. Scattered light member 23 of monitoring device 22 is located outside measuring chamber 12, namely, in the beam direction behind measuring chamber 12 and ahead of radiation absorber 14 in monitoring position 32. No scattered light member 21 is used for the monitoring measurement in first accommodation device 16 in calibrating position 31.

In the second exemplary embodiment, in FIG. 2, inside measuring chamber 12, next to first accommodation device 16, in the beam direction, there is situated a second accommodation device 18. First accommodation device 16 is located in calibrating position 31, and is used for accommodating scattered light member 21 of the calibrating device. Second accommodation device 18 is located in monitoring position 32, and is used for accommodating additional scattered light member 23 of monitoring device 22. No scattered light member 21 is used for the monitoring measurement in first accommodation device 16 in calibrating position 31.

In the third exemplary embodiment, in FIG. 3, inside measuring chamber 12, a positioning device 19 is provided, using which, for example, the same scattered light member 21 is displaceable from calibrating position 31 to monitoring position 32 for the monitoring measurement, and there it takes over the function of additional scattered light member 23 of monitoring device 22. One may also, however, displace additional scattered light member 23 of monitoring device 22 from monitoring position 32 to calibrating position 31 for the calibrating, so that then scattered light member 23 takes over the function of scattered light member 21.

With regard to the exemplary embodiments in FIG. 2 or 3, measuring chamber 12 is expediently configured to have accommodation devices 16, 18 or positioning device 19, into which scattered light member 21 of the calibrating device and additional scattered light member 23 of monitoring device 22 may be introduced, and stopped there, or scattered light member 23 is able to be positioned. Thereby scattered light member 23 of monitoring device 22 obtains a defined monitoring position 32 within measuring chamber 12 and, upon irradiation by light beam 11b of light source 10, it generates a defined scattered light pattern having scattered radiation 30, which is recorded by additional light sensor 24 and is evaluated by evaluation device 25 as a monitoring measurement. The signal of additional evaluation device 25 is supplied to microcontroller 33. Based on the defined physical properties of scattered light member 23 in defined monitoring position 32, and the defined situation of light sensor 24, on the one hand, the intensity of light beam 11b, that is relevant for the particulate measurement, in measuring chamber 12 is ascertained and monitored, and on the other hand, using the result of the monitoring measurement, the result of one or more particulate measurements carried out between the monitoring measurements is automatically corrected.

If a calibrating measurement and a first monitoring measurement are carried out one directly after the other, and the value of the first monitoring measurement is stored as a reference value, every subsequent monitoring measurement is able to be returned, using the reference value, directly to the calibrating measurement and the calibration state.

On the other hand, the intensity of light beam 11b may be regulated to the calibration state using the result of each monitoring measurement and the known reference value. Before each particulate measurement, if a monitoring measurement having a regulation of the intensity of light beam 11b is carried out, one may do without a correction calculation of the measuring results.

By a calibration that is carried out in the case of different scattered light intensities using different scattered light members, the measuring unit is able to be calibrated in a broad intensity range, so that it supplies measuring results having a particularly great accuracy over a broad intensity range.

Because of monitoring device 22, the recording and monitoring and/or regulating is carried out of the intensity of light beam 11b of light source 10 that is relevant to the particulate measurement. With that, it becomes possible, on the one hand, to record and monitor soiling or aging of all optical components in the optical path between light source 10 and the particulate concentration to be measured in measuring chamber 12, and on the other hand, using the result of the monitoring measurement, automatically to correct the result of a particulate measurement carried out to the calibration state. For this purpose, monitoring device 22 may be used either permanently or only from time to time, directly before and directly after an exhaust gas measurement.

On the other hand, soiling or aging of all optical components in the optical path between light source 10 and the particulate concentration to be measured in measuring chamber 12 is basically able to be eliminated by an appropriate regulation of the intensity of light beam 11b. Before each particulate measurement, if a monitoring measurement having a regulation of the intensity of light beam 11b is carried out, one may do without a correction calculation of the measuring results.

In the exemplary embodiments in FIG. 1 and FIG. 2, in evaluation device 25 or in microcontroller 33 a sequence control is provided, using which the provided measuring conditions are made secure without exhaust gas, without scattered light member 21 in calibrating position 31 and having properly positioned scattered light member 23 in monitoring position 32.

In the exemplary embodiment in FIG. 3, in microcontroller 33 or in evaluation device 25, an additional sequence control is provided, using which the positioning of additional scattered light member 23 is undertaken within measuring chamber 12, and the provided measuring conditions are made secure without exhaust gas.

In this context, the sequence control is able to take into account the following conditions:
If A) is satisfied
before the start of the particulate measurement in time, and
measuring chamber 12 without exhaust gas and
scattered light member 23 in monitoring position 32,
or if B) is satisfied
after the particulate measurement in time, and
measuring chamber 12 without exhaust gas and
scattered light member 23 in monitoring position 32,
in response to switched-on light source 10 the intensity of light beam 11*b* is recorded with the aid of scattering radiation 30 having additional light sensor 24.

In case A, using the signal of light sensor 24 before the particulate measurement, the intensity of light source 10 is regulated to the calibrating state. For this purpose, the control loop mentioned is provided.

In case B, the measurement of the intensity of scattered radiation 30 may take place after the particulate measurement, in order to detect a possible drift during the exhaust gas measurement and, if necessary, to correct the result of the particulate measurement to the calibration state, using a correction calculation. The mathematical description of the correction calculations is implemented in a computer program, and is carried out by an additional microcontroller present in the measuring unit before the output of the values for the exhaust gas measurement.

What is claimed is:

1. A measuring unit for measuring a particulate concentration in exhaust gases using scattered light, comprising:
   a measuring chamber having at least one light source and having at least one light sensor, the measuring chamber being situated in an optical path of the light source, the light source configured to generate a light beam, which runs in the measuring chamber as a chamber light beam, the light sensor being configured to record the light of the chamber light beam that is scattered in the measuring chamber by particulates of the exhaust gas; and
   a monitoring device to detect an intensity of the chamber light beam in the measuring chamber with the aid of scattered radiation; and
   at least one evaluation device to determine the particulate concentration associated with a scattered light member;
   wherein the monitoring device includes the scattered light member and at least one additional light sensor, and wherein in response to the irradiation using the light beam, the scattered light member generates scattered radiation and the additional light sensor records the scattered radiation generated by the scattered light member,
   wherein the scattered light member generates defined scattering radiation,
   wherein at a defined intensity of the light beam, the scattered light member supplies the defined scattering radiation at a defined intensity,
   wherein the at least one light source is a laser light source to generate the light beam which is coupled into the measuring chamber using the defined intensity and runs within the measuring chamber as the chamber light beam, which exits from the measuring chamber as an output light beam which impinges upon a radiation absorber, in which non-scattered or partially absorbed light of the light source is completely absorbed or nullified, and
   wherein the scattered light member is settable into a calibrating device or a scattered light member of a present calibrating device is settable into the monitoring device as the scattered light member,
   wherein there are light sensors in the measuring unit and the at least one evaluation device, so that the light scattered by the scattered light member in the measuring chamber is recordable having scattered light radiations by the light sensors and the particulate concentration associated with the scattered light member is ascertained by the at least one evaluation device, and
   wherein the light source and/or the at least one evaluation device is adjustable so that a specified, known particulate concentration as a result of the calibrating measurement is outputtable by the at least one evaluation device.

2. The measuring unit of claim 1, wherein the scattered light member is situated in a monitoring position in the beam direction of the light source outside the measuring chamber.

3. The measuring unit of claim 1, wherein the scattered light member is situated in a monitoring position within the measuring chamber.

4. The measuring unit of claim 1, further comprising:
   a positioning device in the measuring chamber, using which the scattered light member is displaceable from a calibrating position to a monitoring position.

5. The measuring unit of claim 1, further comprising:
   an additional evaluation device for ascertaining and/or representing the scattered radiation recorded by the additional light sensor and which is assigned to the additional light sensor.

6. The measuring unit of claim 1, further comprising:
   a microcontroller, which compares the scattered radiation recorded by the additional light sensor and ascertained by the additional evaluation device to a specified reference value for the scattered radiation.

7. The measuring unit of claim 6, wherein the microcontroller is connected to the additional evaluation device and the light source and includes a control system which regulates the intensity of the light source to the specified reference value of the scattered radiation.

8. The measuring unit of claim 6, wherein the microcontroller is connected to the additional evaluation device and the evaluation devices, and wherein the result of the exhaust gas measurement is corrected.

9. The measuring unit of claim 8, wherein the microcontroller has a correction algorithm, and wherein by using the correction algorithm, the result of the evaluation devices is corrected with the aid of the deviation of the ascertained intensity of the scattered radiation from the specified reference value of the scattered radiation.

10. The measuring unit of claim 1, further comprising:
    a first accommodation device in a calibrating position, which is for accommodating the scattered light member of the calibrating device; and
    a second accommodation device in a monitoring position, which is for accommodating an additional scattered light member of the monitoring device.

11. A method for monitoring a measuring unit for measuring a particulate concentration in exhaust gases, the method comprising:

measuring, using a measuring unit, the particulate concentration in the exhaust gases using scattered light, wherein the measuring unit includes a measuring chamber having at least one light source and having at least one light sensor, the measuring chamber being situated in an optical path of the light source, the light source configured to generate a light beam, which runs in the measuring chamber as a chamber light beam, the light sensor being configured to record the light of the chamber light beam that is scattered in the measuring chamber by particulates of the exhaust gas, and includes a monitoring device to detect an intensity of the chamber light beam in the measuring chamber with the aid of scattered radiation; and taking a monitoring measurement to detect the intensity of the light beam running in the measuring chamber; and determining, via at least one evaluation device, the particulate concentration associated with a scattered light member;

wherein in response to the irradiation using the light beam, the scattered light member generates scattered radiation and an additional light sensor records the scattered radiation generated by the scattered light member, wherein the scattered light member generates defined scattering radiation, and wherein at a defined intensity of the light beam, the scattered light member supplies the defined scattering radiation at a defined intensity, and wherein the at least one light source is a laser light source to generate the light beam which is coupled into the measuring chamber using the defined intensity and runs within the measuring chamber as the chamber light beam, which exits from the measuring chamber as an output light beam which impinges upon a radiation absorber, in which non-scattered or partially absorbed light of the light source is completely absorbed or nullified, and wherein the scattered light member is settable into a calibrating device or a scattered light member of a present calibrating device is settable into the monitoring device as the scattered light member, wherein there are light sensors in the measuring unit and the at least one evaluation device, so that the light scattered by the scattered light member in the measuring chamber is recordable having scattered light radiations by the light sensors and the particulate concentration associated with the scattered light member is ascertained by the at least one evaluation device, and wherein the light source and/or the at least one evaluation device is adjustable so that a specified, known particulate concentration as a result of the calibrating measurement is outputtable by the at least one evaluation device.

12. The method of claim 11, wherein a generated scattered radiation is ascertained by the monitoring device, and wherein the intensity of the light beam in the measuring chamber is monitored and/or regulated with the aid of a comparison of the ascertained scattered radiation to the reference value for the scattered radiation.

13. The method of claim 11, wherein the light intensity of the light source is corrected so that the ascertained intensity of the scattered radiation is corrected to the specified reference value of the scattered radiation.

14. The method of claim 11, wherein the result of the measurement of the particulate concentration is corrected with the aid of the deviation of the ascertained intensity of the scattered radiation from the specified reference value for the scattered radiation.

15. The method of claim 11, wherein the scattered light member is situated in a monitoring position in the beam direction of the light source outside the measuring chamber.

16. The method of claim 11, wherein the scattered light member is situated in a monitoring position within the measuring chamber.

17. The method of claim 11, further comprising:
using a positioning device in the measuring chamber so that the scattered light member is displaceable from a calibrating position to a monitoring position.

18. The method of claim 11, further comprising:
ascertaining and/or representing, using an additional evaluation device, the scattered radiation recorded by an additional light sensor and which is assigned to the additional light sensor.

19. The method of claim 11, further comprising:
comparing, using a microcontroller, the scattered radiation recorded by the additional light sensor and ascertained by an additional evaluation device to a specified reference value for the scattered radiation.

20. The method of claim 19, wherein the microcontroller is connected to the additional evaluation device and the light source and includes a control system which regulates the intensity of the light source to the specified reference value of the scattered radiation.

21. The method of claim 19, wherein the microcontroller is connected to the additional evaluation device and the evaluation devices, and wherein the result of the exhaust gas measurement is corrected.

22. The method of claim 21, wherein the microcontroller has a correction algorithm, and wherein by using the correction algorithm, the result of the evaluation devices is corrected with the aid of the deviation of the ascertained intensity of the scattered radiation from the specified reference value of the scattered radiation.

23. The method of claim 11, wherein there is a first accommodation device in a calibrating position, which is for accommodating the scattered light member of the calibrating device; and wherein there is a second accommodation device in a monitoring position, which is for accommodating an additional scattered light member of the monitoring device.

* * * * *